United States Patent [19]

Howe

[11] 4,140,515

[45] Feb. 20, 1979

[54] ARYL-3-ISOXAZOLE BENZOATES AS PLANT GROWTH REGULANTS AND HERBICIDES

[75] Inventor: Robert K. Howe, Bridgeton, Mo.

[73] Assignee: Monsanto Company, St. Louis, Mo.

[21] Appl. No.: 796,295

[22] Filed: May 12, 1977

[51] Int. Cl.$^2$ .................. C07D 261/08; A01N 9/28
[52] U.S. Cl. ................................. 71/88; 71/74; 71/76; 71/94; 260/307 H; 260/566 A; 260/566 D; 546/275
[58] Field of Search .............. 260/307 H; 71/76, 88, 71/74

[56] References Cited

U.S. PATENT DOCUMENTS

| | | | |
|---|---|---|---|
| 3,192,103 | 6/1965 | Sousa et al. | 167/33 |
| 3,211,742 | 10/1965 | Lenaers | 260/307 |
| 3,772,284 | 11/1973 | Singh et al. | 260/239 A |
| 3,882,138 | 5/1975 | Brouwer et al. | 260/307 G |
| 3,947,263 | 3/1976 | Brouwer et al. | 71/76 |
| 3,987,179 | 10/1976 | Nadelson | 424/272 |
| 4,032,644 | 6/1977 | Nadelson | 424/272 |

FOREIGN PATENT DOCUMENTS

| | | |
|---|---|---|
| 837454 | 7/1976 | Belgium. |
| 2426878 | 8/1976 | Fed. Rep. of Germany. |

OTHER PUBLICATIONS

Katlkar – Phytochemistry 15, 1421–1424 (1976).
Harsonyi et al. – C.A. 68, 95829t (1968).
Brown et al. – Pesticide Science 4, 473–484 (1973).

*Primary Examiner*—Raymond V. Rush
*Attorney, Agent, or Firm*—Richard H. Shear; Donald W. Peterson

[57] ABSTRACT

2-(5-Aryl or substituted aryl-3-isoxazolyl) benzoic acids or benzoates, e.g., 2-[5-[3-(trifluoromethyl)phenyl]-3-isoxazolyl] benzoic acid, and to their method of use as herbicides and plant growth regulants as well as to agricultural chemical compositions thereof.

16 Claims, No Drawings

ARYL-3-ISOXAZOLE BENZOATES AS PLANT GROWTH REGULANTS AND HERBICIDES

The invention relates to novel isoxazoles as well as their use as agricultural chemicals. The novel compounds have been found to be effective in inhibiting the growth of undesirable vegetation. At lower rates, the compounds have been found to be effective in regulating the growth of desirable plants.

The compounds of the invention may be represented by the following chemical formula

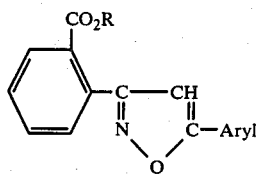

wherein R is selected from the group consisting of hydrogen, lower alkyl and agriculturally acceptable cations.

The term "Aryl" as used herein is understood to include pyridyl.

In accordance with the novel aspects of the invention, the isoxazoles may be prepared in accordance with the following.

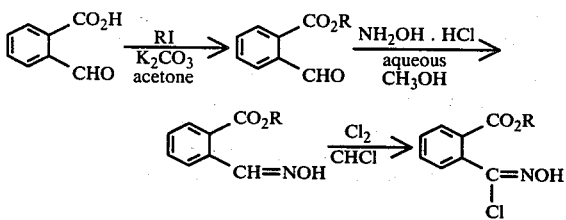

As is apparent to those skilled in the art, o-formylbenzoates may be prepared by known techniques. Addition of hydroxylamine hydrochloride in aqueous methanol results in 2-(hydroxyiminomethyl) benzoates which can be converted to the appropriate esters of benzohydroxamoyl chloride by the addition of chlorine in chloroform. Reaction of the appropriate esters of benzohydroxamoyl chloride with an olefinic or acetylenic benzene results in either the isoxazole or crude isoxazolines that may be converted to isoxazoles by treatment with N-bromosuccinimide or dichlorodicyanobenzoquinone.

In accordance with the the above procedure and by way of example thereof, the following examples are presented.

EXAMPLE 1

Preparation of o-Methoxycarbonylbenzohydroxamoyl Chloride.

Methyl o-formylbenzoate was prepared in 81% yield from 2-carboxybenzaldehyde by the procedure of Brown and Sargent, *Journal Chemical Society*, P 1818 (1969). A solution of 1.64 g (0.010 mol) of methyl o-formylbenzoate and 1.05 g (.015 mol) of hydroxylamine hydrochloride in 95 ml of 30% aqueous methanol was stirred at 23° C. for 50 minutes and then was cooled in ice. Scratching induced crystallization of 0.70 g of white solid (mp 73–74.5° C.) which was methyl 2-(hydroxyiminomethyl) benzoate. Chlorine gas was slowly bubbled into a solution of 7.87 g (.0439 mol) of methyl 2-(hydroxyiminomethyl)benzoate in 250 ml of $CHCl_3$ stirred at 0° C. (ice-methanol bath). A blue color formed, and the clear solution became cloudy. Within a few minutes, the blue reaction mixture turned green. After about 20 minutes, excess chlorine gas began to come through the solution, so chlorine addition was stopped and the solution was stirred in an ice bath for 1 hour until the green color had nearly all faded. Nitrogen gas was bubbled through the solution as it was allowed to warn to 20° C. during 30 minutes. The solution was concentrated under aspirator vacuum at 30–40° C. The residue was triturated with 50 ml of ether, and the supernatant was decanted from a little insoluble gum and was concentrated to 7.21 g of viscous oil. This compound was identified as o-methoxycarbonylbenzohydroxamoyl chloride.

EXAMPLE 2

Preparation of Methyl 2-(5-Phenyl-3-Isoxazolyl)Benzoate.

To a solution of 7.0 g (.0329 mol) of o-methoxycarbonylbenzohydroxamoyl chloride and 6.74 g (.066 mol) of ethynylbenzene in 200 ml of ether was added dropwise a solution of 3.32 g (.033 mol) of triethylamine in 50 ml of ether during 35 minutes with stirring at $-5$ to 0° C. The mixture was stirred at $-5$ to 0° C. for another 30 minutes and then was allowed to warm to 20° C. during 1 hour with stirring. The reaction mixture was washed twice with water, dried ($CaSO_4$), and concentrated under vacuum to 90° C. at 20 torr to 7.52 g of oil. Chromatography of the oil on silica gel (Woelm for dry column chromatography) with benzene gave 4.14 g of product, mp 62–67° C. Crystallization of 1.0 g of this solid from methanol at 0° C. gave 0.9 g of white solid, mp 68–69.5° C.

Anal. Calc"d. for $C_{17}H_{13}NO_3$: C, 73.11; H, 4.69; N, 5.02. Found: C, 73.22; H, 4.45; N, 4.99.

EXAMPLE 3

Preparation of Methyl 2-[5-(4-Chlorophenyl)-3-Isoxazolyl]Benzoate.

To a stirred solution of 10.7 g (.050 mol) of o-methoxycarbonylbenzohydroxamoyl chloride and 13.9 g (.10 mol) of p-chlorostyrene in 150 ml of ether was added dropwise 5.25 g (.052 mol) of triethylamine in 20 ml of ether during 45 minutes with stirring at 0–5° C. The mixture was stirred at 20° C. for 20 hours and then extracted with three 100-ml portions of water; the ether layer was dried ($CaSO_4$) and concentrated under vacuum to 85° C. at 0.2 torr to give 12.1 g (77% yield) of crude isoxazoline. This material (about 0.0383 mol), 6.9 g (.0383 mol) of N-bromosuccinimide, and a trace of benzoyl peroxide in 150 ml of $CCl_4$ was held at reflux for 1 hour and 10 minutes, allowed to cool, filtered, and concentrated under vacuum to 12.8 g of oil. The oil was crystallized from methanol to give 5.0 g of yellow solid, mp 81–112° C. Trituration of the solid with 200 ml of ether and filtration gave 0.22 g of insoluble yellow solid, mp 202–204° C. (unidentified). Concentration of the ether filtrate gave 4.70 g of pale yellow solid, mp 83–85° C. This solid was crystallized from heptane (charcoal) to give 3.3 g of the desired product as a white solid, mp 85–86° C.

Anal. Calc'd. for $C_{17}H_{12}ClNO_3$: C, 65.08; H, 3.86; N, 4.46. Found: C, 65.06; H, 3.67; N, 4.34.

EXAMPLE 4

Preparation of Methyl 2-[5-(4-Methoxyphenyl)-3-Isoxazolyl]Benzoate.

To a solution of 7.50 g (.0351 mol) of o-methoxycarbonylbenzohydroxamoyl chloride and 9.4 g (.070 mol) of p-methoxystyrene in 100 ml of ether stirred at 0–5° C. was added dropwise a solution of 3.74 g (.037 mol) of triethylamine in 15 ml of ether during 30 minutes. The mixture was stirred at 0° C. for 1 hour and at 20° C. for 70 hours and then was extracted with three 100-ml portions of water. The ether layer was dried (CaSO$_4$) and concentrated under vacuum to 90° C. at 20 torr and then on a Kugelrohr to 80° C. at 0.05 torr. The pot residue, 7.52 g of viscous oil, appeared to be about 90% pure isoxazoline.

A mixture of 6.2 g (about 0.0199 mol) of the crude isoxazoline and 9.08 g (.04 mol) of dichlorodicyanobenzoquinone in 50 ml of chlorobenzene was held at reflux for 2.5 hours, was allowed to cool, was filtered free of 3.8 g of dichlorodicyanohydroquinone (ir identification), and was concentrated under vacuum to 11.3 g of black solid. This material was chromatographed on 250 g of silica gel (Woelm for dry column chromatography) with benzene. After 420 ml of eluate had been collected, the desired product, 4.55 g, mp 96.5–98° C., was obtained in the next 500 ml of eluate. Crystallization of the solid from hexane and then methanol gave 3.28 g (53%) of white solid, mp 97–98.5° C.

Anal. Calc'd. for $C_{18}H_{15}NO_4$: C, 69.89; H, 4.89; N, 4.53. Found: C, 69.88; H, 4.98; N, 4.38.

EXAMPLE 5

Preparation of Methyl 2-[5-(3-Trifluoromethyl)Phenyl-3-Isoxazolyl]Benzoate.

To a solution of 12.3 g (.0714 mol) of m-trifluoromethylstyrene and 15.6 g (.073 mol) of o-methoxycarbonylbenzohydroxamoyl chloride in 200 ml of ether stirred at 0–5° C. was added dropwise a solution of 9.43 g (.073 mol) of ethyldiisopropylamine in 35 ml of ether during 45 minutes. The mixture was stirred at 0–5° C. for another 2 hours and then at 20° C. for 3 hours. Ether, 50 ml, was added, and the mixture was extracted three times with 200-ml portions of water. The ether layer was dried (CaSO$_4$) and concentrated under vacuum to 90° C. at 0.5 torr to give 18.4 g of residual oil which was identified as methyl 2-[5-[3-(trifluoromethyl)phenyl]-2-isoxazolin-3-yl]-benzoate.

A mixture of 14.2 g (0.0407 mol) of methyl 2-[5-[3-(trifluoromethyl)phenyl]-2-isoxazolin-3-yl]benzoate, 7.26 g (.0408 mol) of N-bromosuccinimide, and 0.3 g of benzoyl peroxide in 150 ml of carbon tetrachloride was heated at reflux for 4 hours, cooled, filtered, and concentrated under vacuum to 14.5 g of oil. Kugelrohr distillation gave about 89% pure product at 158–160° C. (0.1 torr), which was redistilled to give 9.8 g (70%) of 97% pure product at 148° C. (0.1 torr).

Anal. Calc'd. for $C_{18}H_{12}F_3NO_3$: C, 62.25; H, 3.48; N, 4.03. Found: C, 62.27; H, 3.50; N, 4.09.

EXAMPLE 6

Preparation of Methyl 2-[5-(2-Pyridyl)-3-Isoxazolyl]-Benzoate.

A solution of 7.38 g (.0702 mol) of 2-vinylpyridine and 9.07 g (.0702 mol) of ethyldiisopropylamine in 60 ml of ether was added dropwise during 20 minutes to a solution of 15.0 g (0.0702 mol) of o-methoxycarbonylbenzohydroxamoyl chloride in 200 ml of ether stirred at 0–5° C. The mixture was stirred at 0–5° C for another two hours and then at 20° C for 24 hours and then was washed twice with aqueous NaHCO$_3$ solution and once with aqueous NaCl solution. The ether layer was dried (CaSO$_4$) and analyzed by ir, which revealed some nitrile oxide to be left. The ether solution was allowed to stand another 48 hours and then was concentrated to 90° C at 0.15 torr to give 14.23 g of viscous oil, methyl 2-[5-(2-pyridyl)-2-isoxazolin-3-yl]benzoate.

A mixture of 11.0 g (.039 mol) of methyl 2-[5-(2-pyridyl)-2-isoxazolin-3-yl]benzoate and 9.76 g (.043 mol) of 2,3-dichloro-5,6-dicyano-1,4-benzoquinone in 200 ml of chlorobenzene was held at reflux for 3 hours; the mixture was allowed to cool, was filtered, and was concentrated under vacuum to 12.0 g of residue. The residue was chromatographed on 400 g of silica gel with 20% ether in benzene to give 3.8 g (35%) of solid, mp 54–57° C. Recrystallization of a small sample gave solid with mp 58–60.5° C.

Anal. Calc'd. for $C_{16}H_{12}N_2O_3$: C, 68.56; H, 4.32; N, 9.99. Found: C, 68.41; H, 4.35; N, 9.93.

Acids may be prepared by hydrolysis of the appropriate ester.

EXAMPLE 7

Preparation of 2-[5-(4-Chlorophenyl)-3-Isoxazolyl]Benzoic Acid.

A mixture of 2.8 g of methyl 2-[5-(4-chlorophenyl)3-isoxazolyl]benzoate, 12 ml of concentrated HCl, and 14 ml of acetic acid was held at reflux for 4 hours, cooled, diluted with water, and filtered to give 2.55 g (95%) of white solid, mp 174–176° C. Recrystallization of the solid gave 2.18 g of solid, mp 175.5–177.5° C.

Anal. Calc'd. for $C_{16}H_{10}ClNO_3$: C, 64.12; H, 3.36. Found: C, 63.98; H, 3.40.

EXAMPLE 8

Preparation of 2-[5-(4-Methoxyphenyl)-3-Isoxazolyl]-Benzoic Acid.

A solution of 1.81 g of methyl 2-[5-(4-methoxyphenyl)-3-isoxazolyl]benzoate in 8 ml concentrated HCl and 8 ml of acetic acid was held at reflux for 4 hours, cooled, diluted with water, and filtered to give 1.71 g (99%) of white solid, mp 182–185° C. Recrystallization of the solid from CH$_3$CN gave 1.27 g (73%) of solid, mp 186–187.5° C.

Anal. Calc'd. for $C_{17}H_{13}NO_4$: C, 69.15; H, 4.44. Found: C, 69.11; H, 4.44.

EXAMPLE 9

Preparation of 2-[5-[3-(Trifluoromethyl)Phenyl]-3-Isoxazolyl]Benzoic Acid.

A 9.8 g sample of methyl 2-]5-[3(trifluoromethyl)phenyl]-3-isoxazolyl]benzoate in benzene was allowed to stand on an Activity I alumina column for three days. Elution of the column with glacial acetic acid gave 15 g of solid. This solid was added to dilute HCl, and the solution was extracted with ether. Concentration of the ether gave 3.8 g of solid, which was recrystallized from aqueous ethanol to give 3.0 g of solid acid, mp 165–167° C.

Anal. Calc'd. for $C_{17}H_{10}F_3NO_3$: C, 61.27; H, 3.02; N, 4.20. Found: C, 61.05; H, 3.02; N, 4.24.

EXAMPLE 10

Preparation of 2-(5-Phenyl-3-Isoxazolyl)Benzoic Acid.

A solution of 1.0 g of ester was heated in 4 ml of acetic acid and 4 ml of concentrated HCl at reflux for 4 hours and was concentrated under vacuum. The solid residue was triturated with water, collected, and dried to give 0.85 g of solid, mp 144–147° C. Recrystallization of this solid from benzene gave 0.70 g of white solid, mp 147.5–149° C.

Anal. Calc'd. for $C_{16}H_{11}NO_3$: C, 72.45; H, 4.18; N, 5.28. Found: C, 72.60; H, 4.14; N, 5.22.

Salts may be prepared in accordance with Examples 11 and 12.

EXAMPLE 11

Preparation of The Triethanolamine Salt of 2-[5-(4-Chlorophenyl)-3-Isoxazolyl]Benzoic Acid.

To a solution of 0.9705 g (.00324 mol) of the acid in 75 ml of ethyl acetate was added a solution of 0.483 g (.00324 mol) of triethanolamine in 15 ml of ethyl acetate. Seed crystals (obtained from an aliquot diluted with ether) were added to promote crystallization; 1.20 g of white solid, mp 96.5–97.5° C.

Anal. Calc'd. for $C_{22}H_{25}ClN_2O_6$: C, 58.86; H, 5.61. Found: C, 58.93; H, 5.63.

EXAMPLE 12

Preparation of The Triethanolamine Salt of 2-[5-(4-Methoxyphenyl)-3-Isoxazolyl]Benzoic Acid.

Utilizing the procedure of Example 11, the triethanolamine salt of 2-[5-(4-methoxyphenyl)-3-isoxazolyl]benzoic acid was prepared and was crystallized from ethyl acetate to give a white solid, mp 88–90° C, in 73% yield.

Anal. Calc'd. for $C_{23}H_{28}N_2O_7$: C, 62.15; H, 6.35. Found: C, 62.03; H, 6.37.

In a manner analogous to that described above, the following compounds have been prepared.

| Ex. | Compound |
|---|---|
| 13 | Methyl 2-[5-(1-Naphthyl)-3-Isoxazolyl]Benzoate |
| | Anal. Calc'd. for $C_{21}H_{15}NO_3$: C, 76.58; H, 4.59; N, 4.23. |
| | Found: C, 76.06; H, 4.86; N, 4.09. |
| 14 | Methyl 2-[5-(4-Pyridyl)-3-Isoxazolyl]Benzoate, mp 84–85.5° C. |
| | Anal. Calc'd. for $C_{16}H_{12}N_2O_3$: C, 68.47; H, 4.32. |
| | Found: C, 68.43; H, 4.32. |

Preferred are those isoxazole benzoates in which the Aryl is pyridyl, phenyl or phenyl substituted by one or more halogen, trifluoromethyl, lower alkyl or lower alkoxy moieties.

As used herein, the term "lower alkyl" or "lower alkoxy" is understood to mean those alkyl or alkoxy groups having from 1 to 5 carbon atoms, inclusive.

The term "agriculturally acceptable cations" is understood to mean those cations which are commonly used in herbicidal compositions to form the salt of the free acid, including but not limited to the alkali metal, substituted amine and ammonium cations.

As noted above, the compounds of the present invention have been found to be effective in the partial or total inhibition of undesirable vegetation. Tables I and II summarize results of tests conducted to determine the pre-emergent as well as the post-emergent herbicidal activity of the compounds.

The pre-emergent test was conducted as follows:

A good grade of top soil was placed in aluminum pans and compacted to a depth of three-eighths to one-half inch from the top of the pan. On the top of the soil was placed a predetermined number of seeds or vegetative propagules of various plant species. The soil required to level fill the pans after seeding or adding vegetative propagules was weighed into a pan. A known amount of the active ingredient applied in a solvent or as a wettable powder and the soil were thoroughly mixed, and used as a cover layer for prepared pans. After treatment, the pans were moved into a greenhouse bench where they were watered from below as needed to give adequate moisture for germination and growth.

Unless noted otherwise, approximately 4 weeks after seeding and treating, the plants were observed and the results recorded. The herbicidal rating was obtained by means of a fixed scale based on percent injury of each test species lot. The ratings are defined as follows:

| % Control | Rating |
|---|---|
| 0–24 | 0 |
| 25–49 | 1 |
| 50–74 | 2 |
| 75–100 | 3 |

The post-emergent tests were conducted as follows:

The active ingredients are applied in spray form to two or three-week old specimens of various plant species. The spray, a solution or wettable powder suspension containing the appropriate rate of active ingredient to give the desired test rate and a surfactant, is applied to the plants. The treated plants are placed in a greenhouse and unless otherwise noted approximately four weeks later the effects ranging from partial to total inhibition are observed and recorded. The results are shown in Tables I and II in which the post-emergent herbicidal activity index is as follows:

| % Control | Rating |
|---|---|
| 0–24 | 0 |
| 25–49 | 1 |
| 50–74 | 2 |
| 75–99 | 3 |
| 100 | 4 |

The plants species utilized in these tests are identified by letter in accordance with the following legend:

| | |
|---|---|
| A Soybean | I Hemp Sesbania |
| B Sugarbeet | J Lambsquarters |
| C Wheat | K Smartweed |
| D Rice | L Velvet Leaf |
| E Sorghum | M Bromus Tectorum |
| F Cocklebur | N Panicum Spp. |
| G Wild Buckwheat | O Barnyard Grass |
| H Morning Glory | P Crabgrass |

Table 1

| Compound | WAT* | $\frac{kg}{h}$ | Pre-Emergent Plant Species | | | | | | | | | | | | | | | |
|---|---|---|---|---|---|---|---|---|---|---|---|---|---|---|---|---|---|---|
| | | | A | B | C | D | E | F | G | H | I | J | K | L | M | N | O | P |
| 2 | 4 | 1.12 | 0 | 1 | 0 | 1 | 0 | 0 | 0 | 0 | 1 | 1 | 1 | 0 | 0 | 1 | 1 | 1 |

Table 1-continued

| Compound | WAT* | kg/h | A | B | C | D | E | F | G | H | I | J | K | L | M | N | O | P |
|---|---|---|---|---|---|---|---|---|---|---|---|---|---|---|---|---|---|---|
|   | 4 | 5.60 | 0 | 1 | 1 | 2 | 3 | 0 | 2 | 0 | 2 | 2 | 1 | 3 | 3 | 3 | 2 | 3 |
| 3 | 4 | 1.12 | 0 | 1 | 0 | 1 | 1 | 0 | 0 | 1 | 0 | 0 | 1 | 0 | 0 | 0 | 1 | 0 |
|   | 4 | 5.60 | 2 | 2 | 1 | 2 | 3 | 0 | 2 | 1 | 1 | 2 | 2 | 1 | 1 | 0 | 3 | 0 |
| 4 | 4 | 1.12 | 0 | 1 | 0 | 1 | 0 | 0 | 0 | 1 | 1 | 1 | 0 | 1 | 0 | 1 | 2 | 1 |
|   | 4 | 5.60 | 0 | 2 | 0 | 2 | 0 | 0 | 1 | 1 | 2 | 2 | 1 | 1 | 0 | 2 | 3 | 3 |
| 5 | 4 | 1.12 | 1 | 2 | 1 | 2 | 2 | 0 | 2 | 2 | 2 | 2 | 3 | 1 | 2 | 2 | 3 | 3 |
|   | 4 | 5.60 | 2 | 3 | 2 | 3 | 2 | 2 | 3 | 2 | 2 | 2 | 2 | 2 | 2 | 2 | 3 | 3 |
| 6 | 2 | 1.12 | 1 | 1 | 0 | 1 | 0 | 0 | 0 | 1 | 1 | 1 | 0 | 0 | 0 | 0 | 0 | 1 |
|   | 4 | 5.60 | 2 | 2 | 1 | 2 | 2 | 1 | 0 | 1 | 2 | 2 | 1 | 1 | 0 | 0 | 2 | 2 |
| 9 | 4 | 1.12 | 1 | 2 | 1 | 1 | 1 | 0 | 1 | 2 | 2 | 2 | 2 | 1 | 2 | 0 | 2 | 2 |
|   | 4 | 5.60 | 2 | 2 | 2 | 3 | 2 | 1 | 2 | 2 | 3 | 2 | 3 | 1 | 2 | 1 | 3 | 3 |
| 10 | 4 | 1.12 | 1 | 2 | 0 | 1 | 1 | 0 | 0 | 0 | 1 | 0 | 2 | 2 | 3 | 1 | 1 | 2 |
|   | 4 | 5.60 | 2 | 3 | 1 | 3 | 3 | 0 | 3 | 1 | 3 | 2 | 1 | 3 | 3 | 2 | 3 | 3 |
| 13 | 4 | 1.12 | 0 | 1 | 0 | 0 | 1 | 0 | 1 | 1 | 0 | 1 | 1 | 0 | 1 | 1 | 3 | 3 |
|   | 4 | 5.60 | 0 | 2 | 1 | 2 | 2 | 0 | 2 | 1 | 2 | 1 | 1 | 0 | 2 | 3 | 3 | 3 |

| Compound | WAT* | kg/h | Post-Emergent Plant Species ||||||||||||||||
|---|---|---|---|---|---|---|---|---|---|---|---|---|---|---|---|---|---|---|
|  |  |  | A | B | C | D | E | F | G | H | I | J | K | L | M | N | O | P |
| 2 | 4 | 1.12 | 1 | 1 | 1 | 0 | 1 | 0 | 0 | 0 | 1 | 1 | 0 | 1 | 2 | 1 | 1 | 0 |
|   | 4 | 5.60 | 2 | 1 | 1 | 1 | 2 | 2 | 2 | 0 | 2 | 2 | 3 | 2 | 1 | 1 | 1 | 0 |
| 7 | 4 | 1.12 | 1 | 1 | 0 | 0 | 1 | 0 | 1 | 1 | 2 | 2 | 2 | 1 | 0 | 0 | 0 | 0 |
|   | 4 | 5.60 | 2 | 2 | 1 | 0 | 1 | 1 | 1 | 1 | 4 | 4 | 4 | 2 | 0 | 0 | 0 | 0 |
| 8 | 4 | 1.12 | 1 | 1 | 1 | 1 | 0 | 1 | 1 | 1 | 1 | 2 | 2 | 1 | 0 | 0 | 0 | 0 |
|   | 4 | 5.60 | 2 | 2 | 1 | 1 | 1 | 1 | 1 | 1 | 2 | 4 | 4 | 1 | 1 | 3 | 1 | 1 |

*Weeks after treatment

The compounds were further tested by utilizing the above procedure on the following plant species:

| A | Canada Thistle | G | Nutsedge |
| B | Cocklebur | H | Quackgrass |
| C | Velvet Leaf | I | Johnson Grass |
| D | Morning Glory | J | Downy Brome |
| E | Lambsquarters | K | Barnyard Grass |
| F | Smartweed |  |  |

The results are summarized by Table II.

Table II

| Compound | WAT* | kg/H | Pre-Emergent Plant Species |||||||||||
|---|---|---|---|---|---|---|---|---|---|---|---|---|---|
|  |  |  | A | B | C | D | E | F | G | H | I | J | K |
| 2 | 4 | 11.2 | 3 | 1 | 3 | 1 | 3 | 3 | 2 | 2 | 1 | 2 | 3 |
| 3 | 4 | 11.2 | 1 | 0 | 0 | 1 | 3 | 2 | 0 | 2 | 1 | 2 | 3 |
| 4 | 4 | 11.2 | 3 | 1 | 3 | 1 | 3 | 2 | 3 | 2 | 0 | 2 | 3 |
| 5 | 4 | 11.2 | 2 | 1 | 2 | 2 | 3 | 3 | 2 | 2 | 3 | 3 | 3 |
| 6 | 4 | 11.2 | 3 | 0 | 2 | 1 | 1 | 2 | 0 | 1 | 0 | 0 | 2 |
| 7 | 4 | 11.2 | 1 | 0 | 1 | 0 | 3 | 1 | 0 | 1 | 0 | 0 | 2 |
| 8 | 4 | 11.2 | 2 | 1 | 0 | 1 | 2 | 1 | 0 | 2 | 0 | 1 | 1 |
| 9 | 4 | 11.2 | 3 | 1 | 2 | 2 | 3 | 3 | 1 | 3 | 1 | 2 | 2 |
| 10 | 4 | 11.2 | 2 | 0 | 1 | 0 | 2 | 1 | 1 | 1 | 0 | 1 | 2 |
| 11 | 4 | 11.2 | 0 | 0 | 2 | 0 | 0 | 1 | 0 | 0 | 0 | 0 | 0 |
| 12 | 4 | 11.2 | 1 | 0 | 2 | 1 | 1 | 1 | 0 | 2 | 0 | 2 | 2 |
| 13 | 4 | 11.2 | 3 | 1 | 1 | 1 | 3 | 2 | 1 | 2 | 1 | 1 | 3 |
| 14 | 2 | 11.2 | 1 | 0 | 1 | 1 | 1 | 1 | 0 | 1 | 0 | 0 | 1 |

| Compound | WAT* | kg/h | Post-Emergent Plant Species |||||||||||
|---|---|---|---|---|---|---|---|---|---|---|---|---|---|
|  |  |  | A | B | C | D | E | F | G | H | I | J | K |
| 2 | 4 | 11.2 | 2 | 2 | 2 | 1 | 2 | 2 | 2 | 1 | 1 | 1 | 1 |
| 3 | 4 | 11.2 | 1 | 0 | 1 | 1 | 1 | 1 | 0 | 0 | 1 | 0 | 0 |
| 4 | 4 | 11.2 | 1 | 1 | 1 | 1 | 1 | 1 | 0 | 1 | 0 | 1 | 0 |
| 5 | 4 | 11.2 | 1 | 1 | 1 | 1 | 1 | 1 | 1 | 1 | 1 | 1 | 1 |
| 6 | 4 | 11.2 | 0 | 1 | 1 | 1 | 1 | 1 | 0 | 0 | 0 | 0 | 1 |
| 7 | 4 | 11.2 | 1 | 1 | 1 | 0 | 4 | 4 | 0 | 0 | 0 | 0 | 0 |
| 8 | 4 | 11.2 | 1 | 1 | 1 | 1 | 4 | 4 | 0 | 1 | 1 | 0 | 1 |
| 9 | 4 | 11.2 | 2 | 2 | 1 | 1 | 2 | 2 | 2 | 1 | 1 | 1 | 2 |
| 10 | 4 | 11.2 | 1 | 2 | 2 | 1 | 1 | 0 | 1 | 0 | 0 | 1 | 1 |
| 11 | 4 | 11.2 | 1 | 1 | 1 | 1 | 1 | 2 | 0 | 1 | 0 | 0 | 1 |
| 12 | 4 | 11.2 | 1 | 1 | 1 | 1 | 1 | 1 | 0 | 1 | 0 | 0 | 1 |
| 13 | 4 | 11.2 | 2 | 1 | 1 | 2 | 2 | 1 | 0 | 0 | 0 | 0 | 1 |
| 14 | 4 | 11.2 | 0 | 0 | 1 | 0 | 1 | 1 | 0 | 0 | 0 | 0 | 0 |

*Weeks after treatment

The above tables illustrate one aspect of the present invention. That is, the use of the compounds of the invention to kill or injure undesirable plants, e.g. weeds. Another aspect of the invention, however, is the use of said compounds for the regulation of desirable plant growth especially dicotyledonous plants such as legumes.

As used herein, the regulation of "plant growth or development" is understood to mean the modification of the normal sequential development of a treated desirable plant to agricultural maturity. Such modifications are most readily observed as changes in size, shape, color or texture of the treated plant or any of its parts. Similarly, changes in the quantity of plant fruit or flowers are also quite apparent from visual inspection. The above changes may be characterized as an acceleration or retardation of plant growth, stature reduction, leaf or canopy alteration, increased branching, terminal inhibition, increased flowering, defoliation, increased root growth, increased cold hardiness and the like. While many of these modifications are desirable in and of themselves, most often it is their effect on the economic result that is of most importance. For example, a reduction in stature of the plant permits the growth of more plants per unit area. A darkening of the foliar color may be illustrative of higher chlorophyll activity indicative of improved rate of photosynthesis.

Although the regulation of plant growth in accordance with the present invention may include partial inhibition of plant growth, it does not include the total inhibition or killing of such plants. The present invention contemplates the use of an amount of active ingredient which will modify the normal sequential development of the treated plant to agricultural maturity. Such plant growth regulating amounts may vary, not only with the material selected, but also with the modifying effect desired, the species of plant and its stage of development, the plant growth medium and whether a permanent or a transitory effect is sought. it is, however, well within the skill of the art to determine the amount of active ingredient required.

Modification of the plants may be accomplished by applying the active ingredient to seeds, emerging seedlings, roots, stems, leaves, flowers, fruits or other plant parts. Such application may be made directly to the plant part, or indirectly by application to the plant growth medium. Foliar applications to plants beginning to blossom is preferred.

Utilizing the compounds of the invention as the active ingredient in a plant growth regulating composition, said compounds were found to possess plant growth regulating activity when tested in accordance with the following procedure.

Soybean plants, variety Clark 63, were grown in a greenhouse or a growth chamber to the one-half expanded unifoliate stage. At that time, the plants were treated by dipping the plants into an aqueous solution of the chemical, acetone and a surfactant. After growing the plants for approximately two weeks under cool conditions (11–14° C), the plants were transferred to a greenhouse and grown at 24° C. Approximately four weeks after treatment, the plants were observed and compared with control plants that had been dipped into water containing only the surfactant. Results of those observations are summarized by Table III.

Table III

| Compound | Rate (ppm) | Observations |
|---|---|---|
| 2 | 266 | Stature reduction, axillary bud development, leaf inhibition, inhibition of apical development. |
| 5 | 133 | Stature reduction, axillary bud development, leaf inhibition. |
| 6 | 133 | Stature reduction, axillary bud development, stem distortion, leaf distortion, leaf inhibition, inhibition of apical development. |
| 9 | 133 | Stature reduction, epinasty, stimulation of axillary bud development, leaf inhibition. |
| 13 | 133 | Stature reduction, axillary bud development, leaf inhibition, inhibition of apical development. |
| 14 | 266 | No response. |

Compounds 2, 3, 7 and 10 were further tested as follows.

A number of soybean plants, variety Williams, are grown from seeds in plastic pots in the greenhouse for a period of one week at which time the plants are thinned to one plant per pot. When the second trifoliate leaf (three weeks) is fully expanded, the plants are treated with a solution of the active ingredient in acetone and water. Aqueous Tween 20 is used as a surfactant.

When the fifth trifoliate leaf (four to five weeks) is fully expanded, the treated plants are compared with the non-treated control plants and the observations recorded.

Table IV below summarizes the results and observations made in accordance with the above procedure.

Table IV

| Compound | $\frac{kg}{h}$ | Observations |
|---|---|---|
| 2 | 2.8 | Stature reduction, stem distortion, leaf distortion, leaf alteration, altered canopy. |
|  | 0.56 | Stature reduction, stem distortion, leaf distortion, leaf alteration, altered canopy. |
|  | 0.11 | Leaf alteration; altered canopy. |
| 3 | 2.8 | Stature reduction, axillary bud development, stem distortion, leaf distortion, inhibition of apical development. |
|  | 0.56 | Stature reduction, axillary bud development, leaf distortion, stem distortion, leaf alteration. |
|  | 0.11 | Leaf distortion, leaf alteration, stem distortion, altered canopy. |
| 7 | 2.8 | Stature reduction, leaf distortion, leaf inhibition, altered canopy. |
|  | 0.56 | Stature reduction, leaf distortion, leaf inhibition, altered canopy. |
|  | 0.11 | Leaf alteration, altered canopy. |
| 10 | 2.8 | Stature reduction, axillary bud development, stem distortion, leaf distortion, altered canopy. |
|  | 0.56 | Stature reduction, stem distortion, leaf alteration, axillary bud development, altered canopy. |
|  | 0.11 | No response. |

In selecting the appropriate rate of application of the active ingredient, it will be recognized that precise rates will also be dependent upon the desired response, mode of application, plant variety, soil conditions and various other factors known to those skilled in the art. While a rate of about 0.056 to 5.6 kilos per hectare is preferred, higher rates of up to 56 kilos per hectare may be used, depending upon the factors noted above. In addition, it will be recognized that single or multiple applications may be used to exert the desired response.

The above data illustrate that the compounds of the invention may be used as a herbicide or a plant growth regulant. When used as a herbicide, it is desirable that rates of application above 2.24 kilograms per hectare be utilized. When used to regulate the growth of desirable plants, rates below 5.6 kilograms per hectare especially 0.056 to 3.36 are preferred.

In the practice of the invention, the active ingredient can be used alone or in combination with other pesticides or a material referred to in the art as an adjuvant in either liquid or solid form. To prepare such compositions, the active ingredient is admixed with an adjuvant including diluents, extenders, carriers and conditioning agents to provide compositions in the form of finely-divided particulate solids, granules, pellets, wettable powders, dusts, solutions and aqueous dispersions or emulsions. Thus, the active ingredient can be used with an adjuvant such as a finely-divided particulate solid, a solvent liquid of organic origin, water, a wetting agent, dispersing agent or emulsifying agent or any suitable combination of these.

Illustrative finely-divided solid carriers and extenders which are useful in plant growth regulating compositions of this invention include the talcs, clays, pumice, silica, diatomaceous earth, quartz, Fullers earth, sulfur, powdered cork, powdered wood, walnut flour, chalk, tobacco dust, charcoal and the like. Typical liquid diluents include Stoddard solvent, acetone, alcohols, glycols, ethyl acetate, benzene and the like. The plant growth regulating compositions of this invention, particularly liquids and wettable powders, usually contain one or more surface-active agents in amounts sufficient to render a given composition readily dispersible in water or in oil. The term "surface-active agent" is understood to include wetting agents, dispersing agents, suspending agents and emulsifying agents. Such surface-active agents are well known and reference is made to U.S. Pat. No. 2,547,724, Columns 3 and 4, for detailed examples of the same.

Generally, the active ingredients are applied in the form of a composition containing one or more adjuvants which aid in the application of a uniform distribution of the active ingredient. The application of liquid and particulate solid compositions of the active ingredient can be carried out by conventional techniques utilizing, for example, spreaders, power dusters, boom and hand sprayers and spray dusters. The composition can also be applied from airplanes as a dust or spray.

Compositions of this invention generally contain from about 1 to 99 parts active ingredient, about 1 to 50 parts surface-active agent and about 4 to 94 parts solvents, all parts being by weight based on the total weight of the composition.

Although this invention has been described with respect to specific modifications, the details thereof are not to be construed as limitations, for it will be apparent that various equivalents, changes and modifications may be resorted to without departing from the spirit and scope thereof and it is understood that such equivalent embodiments are intended to be included herein.

What is claimed is:

1. A compound having the formula

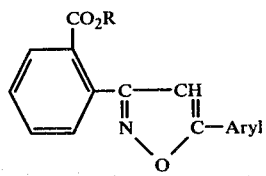

wherein R is selected from the group consisting of hydrogen, lower alkyl and agriculturally acceptable cations; Aryl is selected from the group consisting of phenyl, naphthyl and phenyl substituted by one or more halogen, trifluoromethyl, lower alkyl or lower alkoxy moieties.

2. A compound according to claim 1 wherein Aryl is phenyl or phenyl substituted by one or more halogen, trifluoromethyl, lower alkyl or lower alkoxy moieties.

3. A compound according to claim 1 wherein Aryl is naphthyl.

4. A method for preventing the growth of undesirable vegetation which comprises applying to said vegetation a herbicidally effective amount of a compound having the formula

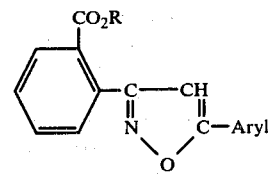

wherein R is selected from the group consisting of hydrogen, lower alkyl and agriculturally acceptable cations; Aryl is selected from the group consisting of phenyl, naphthyl and phenyl substituted by one or more halogen, trifluoromethyl, lower alkyl or lower alkoxy moieties.

5. A method according to claim 4 wherein Aryl is phenyl or phenyl substituted by one or more halogen, trifluoromethyl, lower alkyl or lower alkoxy moieties.

6. A method according to claim 4 wherein Aryl is naphthyl.

7. A method of regulating the growth of desirable plants which comprises applying to said plants an effective amount of a compound having the formula

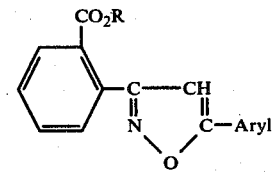

wherein R is selected from the group consisting of hydrogen, lower alkyl and agriculturally acceptable cations; Aryl is selected from the group consisting of phenyl, naphthyl and phenyl substituted by one or more halogen, trifluoromethyl, lower alkyl or lower alkoxy moieties.

8. A method according to claim 7 wherein Aryl is phenyl or phenyl substituted by one or more halogen, trifluoromethyl, lower alkyl or lower alkoxy moieties.

9. A method according to claim 7 wherein Aryl is naphthyl.

10. An agricultural chemical composition comprising from about 1 to about 99 parts by weight of a compound having the formula

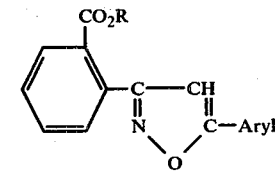

wherein R is selected from the group consisting of hydrogen, lower alkyl and agriculturally acceptable cations; Aryl is selected from the group consisting of phenyl, naphthyl and phenyl substituted by one or more halogen, trifluoromethyl, lower alkyl or lower alkoxy moieties; the remaining part being composed of one or more suitable diluents and/or adjuvants.

11. A composition according to claim 10 wherein Aryl is phenyl or phenyl substituted by one or more halogen, trifluoromethyl, lower alkyl or lower alkoxy moieties.

12. A composition according to claim 10 wherein Aryl is naphthyl.

13. A compound according to claim 1 wherein in said compound Aryl is phenyl substituted by one or more trifluoromethyl moieties.

14. A method according to claim 4 wherein Aryl is phenyl substituted by one or more trifluoromethyl moieties.

15. A method according to claim 7 wherein Aryl is phenyl substituted by one or more trifluoromethyl moieties.

16. An agricultural chemical composition according to claim 10 wherein Aryl is phenyl substituted by one or more trifluoromethyl moieties.

* * * * *